United States Patent
Rickels et al.

(10) Patent No.: US 11,364,125 B2
(45) Date of Patent: Jun. 21, 2022

(54) TAPERED STEM WITH ANTI-ROTATION FEATURES

(71) Applicant: Howmedica Osteonics Corp., Mahwah, NJ (US)

(72) Inventors: Tracy Rickels, Hewitt, NJ (US); Niyati Dave, Gurgaon (IN); Alvin Perez, Ringwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 16/918,361

(22) Filed: Jul. 1, 2020

(65) Prior Publication Data

US 2021/0007852 A1   Jan. 14, 2021

Related U.S. Application Data

(60) Provisional application No. 62/871,374, filed on Jul. 8, 2019.

(51) Int. Cl.
*A61F 2/32* (2006.01)
*A61F 2/36* (2006.01)
*A61F 2/30* (2006.01)

(52) U.S. Cl.
CPC .......... *A61F 2/3609* (2013.01); *A61F 2/3662* (2013.01); *A61F 2002/30214* (2013.01);
(Continued)

(58) Field of Classification Search
CPC ........ A61F 2/3609; A61F 2/3662; A61F 2/32; A61F 2/40; A61F 2002/3625;
(Continued)

(56) References Cited

U.S. PATENT DOCUMENTS 3,996,625 A   12/1976  Noiles
4,404,693 A   9/1983   Zweymuller
(Continued)

FOREIGN PATENT DOCUMENTS

EP   0677281 A2   10/1995
EP   0709071 A2   5/1996
(Continued)

OTHER PUBLICATIONS

Zimmer—ZMR Revision Hip System Surgical Technique; pp. 1-68; Jun. 15, 2015 (Year: 2015).*
(Continued)

*Primary Examiner* — Dinah Baria
(74) *Attorney, Agent, or Firm* — Lerner, David, Littenberg, Krumholz & Mentlik, LLP

(57) ABSTRACT

An intramedullary stem prosthesis includes a trunnion tapered in a first direction toward a proximal end of the intramedullary stem, and a conical shaft interfacing with the trunnion at a modular taper junction. The conical shaft is tapered in a second direction toward a distal end of the second component and has a proximal portion, a distal portion, and flutes positioned about a longitudinal axis of the conical shaft and extending along an entire length of the conical shaft and terminating at the modular taper junction such that the flutes intersect the modular taper junction. The proximal portion defines a first taper angle, the distal portion defines a second taper angle greater than the first taper angle, and the flutes define a major diameter of the conical shaft. The major diameter tapers at a major diameter taper angle that is constant along the entire length of the conical shaft.

20 Claims, 5 Drawing Sheets

(52) U.S. Cl.
CPC ............... *A61F 2002/30604* (2013.01); *A61F 2002/30884* (2013.01); *A61F 2002/365* (2013.01); *A61F 2002/3625* (2013.01)

(58) Field of Classification Search
CPC ........ A61F 2002/365; A61F 2002/3652; A61F 2002/3662; A61F 2002/3678; A61F 2002/30604; A61F 2002/30214; A61F 2002/30884

See application file for complete search history.

(56) References Cited

U.S. PATENT DOCUMENTS

| | | | |
|---|---|---|---|
| 4,549,319 | A | 10/1985 | Meyer |
| 5,002,578 | A | 3/1991 | Luman |
| 6,146,424 | A | 11/2000 | Gray, Jr. et al. |
| 6,520,994 | B2 | 2/2003 | Nogarin |
| 6,702,824 | B2 | 3/2004 | Maroney et al. |
| 6,911,048 | B2 | 6/2005 | Fernandez et al. |
| 6,994,731 | B2 | 2/2006 | Howie |
| 7,044,975 | B2 | 5/2006 | Cheal et al. |
| 7,455,695 | B2 | 11/2008 | Khalili et al. |
| 7,468,078 | B2 | 12/2008 | Sederholm et al. |
| 7,572,297 | B2 | 8/2009 | Cheal et al. |
| 7,575,603 | B2 | 8/2009 | Bergin et al. |
| 7,892,290 | B2 | 2/2011 | Bergin et al. |
| 8,066,779 | B2 | 11/2011 | Gibbs et al. |
| 8,157,871 | B2 | 4/2012 | Ries et al. |
| 8,562,690 | B1 | 10/2013 | Dickerson |
| 8,641,773 | B2 | 2/2014 | Bergin et al. |
| 9,687,252 | B2 | 6/2017 | Kelman et al. |
| 9,717,545 | B2 | 8/2017 | Leisinger |
| 2007/0118229 | A1 | 5/2007 | Bergin et al. |
| 2008/0281430 | A1 | 11/2008 | Kelman et al. |
| 2011/0257758 | A1 | 10/2011 | Smith et al. |
| 2015/0342743 | A1 | 12/2015 | Sobky |
| 2018/0000598 | A1 | 1/2018 | Amis et al. |
| 2018/0235763 | A1* | 8/2018 | Meneghini ............ A61F 2/3609 |
| 2018/0333265 | A1 | 11/2018 | Termanini et al. |

FOREIGN PATENT DOCUMENTS

| | | |
|---|---|---|
| EP | 0623321 B1 | 1/1997 |
| EP | 0682924 B1 | 10/1999 |
| WO | 2017151538 A1 | 9/2017 |

OTHER PUBLICATIONS

Acros Modular Femoral Revision System, Cone Proximal Body Surgical Technique, Zimmer Biomet, pp. 1-64.

Restoration Modular Revision Hip System, Surgical Technique, Stryker, pp. 1-32.

* cited by examiner

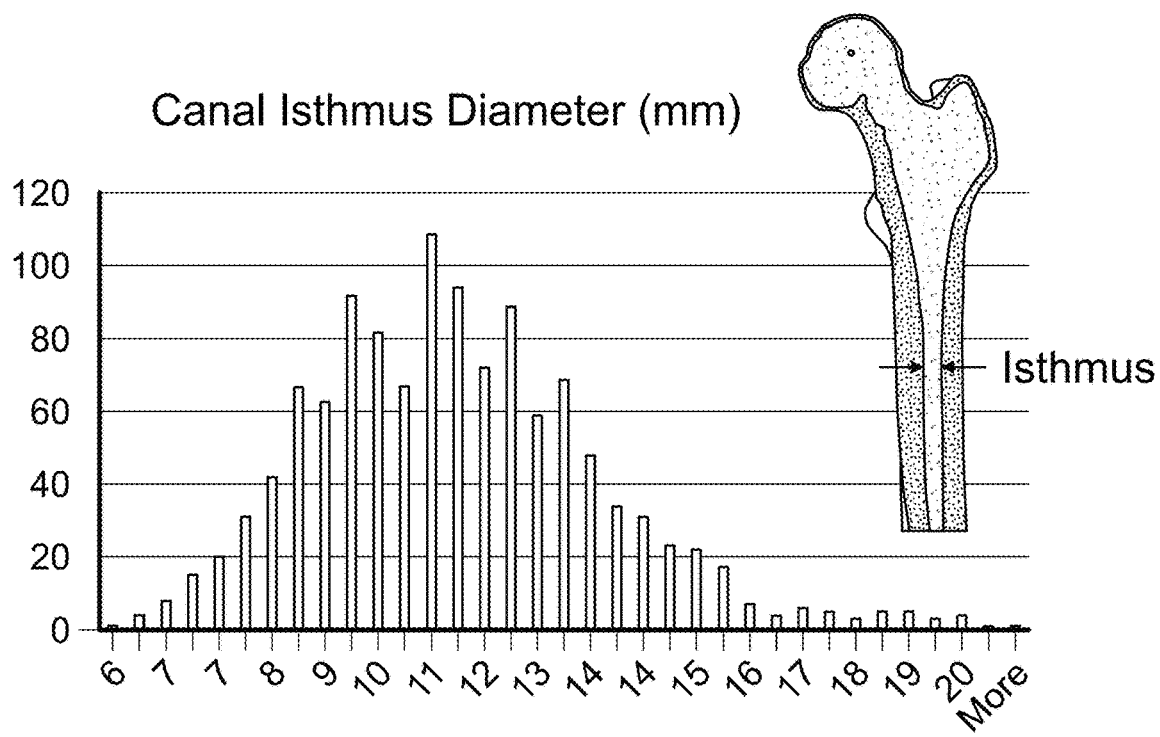
FIG. 1A
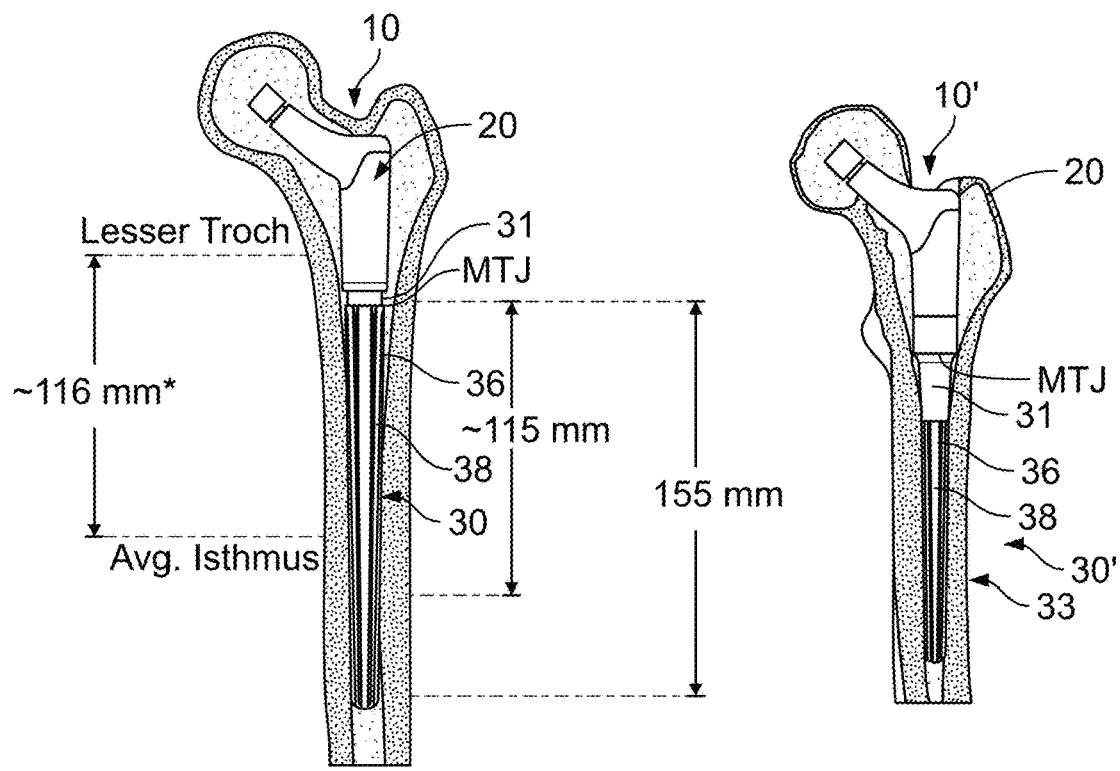
FIG. 1B
(Prior Art)
FIG. 1C
(Prior Art)

TAPERED STEM WITH ANTI-ROTATION FEATURES

CROSS-REFERENCE TO RELATED APPLICATIONS

The application claims the benefit of the filing date of U.S. Provisional Patent Application No. 62/871,374, filed Jul. 8, 2019, the disclosure of which is hereby incorporated herein by reference.

BACKGROUND OF THE INVENTION

Joint replacement procedures generally involve the resection of a native joint surface and replacement of the same with an artificial joint surface. In many of such procedures, such as in hip, knee, and shoulder replacements, the artificial joint surface is stabilized and supported by an intramedullary stem connected thereto which is inserted into an intramedullary canal of a particular bone that is associated with the joint being replaced. Such stems are typically cemented or press-fit to the bone from within the intramedullary canal and receive much of the load applied to the artificial surface. In this regard, intramedullary stems are subjected to significant cyclical stresses particularly as the artificial joint undergoes dynamic movements.

Intramedullary stems can be cemented or press-fit to the bone from within the intramedullary canal. Press-fit stems may require rotational stabilization as the loads applied to the joint surface can cause the stem to rotate within the intramedullary canal potentially compromising the artificial joint. In this regard, some stems include stabilization features in order to provide for rotational stability. One such feature is a fluted shaft in which a shaft of the stem includes a plurality of longitudinally extending flutes or splines that extend along and outwardly from a portion of the length of the shaft and engage the bone from within its canal to prevent rotation relative thereto. FIG. 1B of the present disclosure depicts a modular hip prosthesis 10 that includes an intramedullary stem 30 with a fluted conical shaft 38. The flutes 36 extend along the entire length of the conical shaft 38 and terminate at a modular taper junction ("MTJ") which is defined between a trunnion 31, which receives a modular proximal body 20 of the hip prosthesis, and the conical shaft 38.

However, one drawback to fluted shafts is that they are not particularly resistant to large cyclical fatigue loads. As a result, existing intramedullary stems, particularly those for hip replacements, are not typically offered with fluted shafts in small enough sizes to treat patients with very small femoral canals. FIG. 1A depicts a histogram of femoral canal isthmus diameters for a diverse population of human femoral bones. As shown, isthmus diameters that are 10 mm or less are on the lower end of the distribution and are considered herein to be very small. In this regard, a fluted shaft like that of the prosthesis of FIG. 1B scaled down to fit within a femoral canal having an isthmus of 10 mm or less would be susceptible to failure. One reason for this is that, in order to create the flutes, material is removed between the flutes such that the minor diameter of the shaft (i.e., the cross-sectional dimension of the shaft excluding the flutes) is necessarily reduced to a point that its cross-sectional area is particularly susceptible to fatigue within very small femurs.

In an effort to address this problem, some manufacturers offer modular conical revision hip stems such as the intramedullary stem 30' of the modular prosthesis 10' of FIG. 1C. Intramedullary stem 30' includes a conical shaft 33 that has a fluted section 38 and a fluteless section 31. Fluteless section 31 is located at a proximal end of the conical shaft 33 where stresses are the greatest and has a larger diameter than would be possible if flutes were provided according to conventional designs of larger prostheses. Thus, fluteless section 31 interfaces with the trunnion (not shown) so as to define the MTJ. As such, the flutes 36 of conical shaft 33 terminate well before reaching the MTJ. Therefore, while intramedullary shaft 30' of prosthesis 10' may be sufficient to resist fatigue, the lack of flutes at the proximal end of shaft 33 compromises rotational stability particularly within the region of fluteless section 31. As such, further improvements are desirable.

BRIEF SUMMARY OF THE INVENTION

The present disclosure describes a modular prosthesis that is particularly adapted for use in very small femoral canals, or the canals of any other long bone. The modular prosthesis includes a proximal body and an intramedullary stem. The proximal body is adapted to receive an articular component, such as a femoral head component and includes a tapered opening. The intramedullary stem includes a trunnion adapted to be received within the tapered opening of the proximal body and a conical shaft that is fluted along its entire length. The conical shaft and trunnion are both tapered such that they narrow in opposite directions. The trunnion and conical shaft interface at an MTJ. The conical shaft defines a minor diameter of the stem and has a dual taper such that the conical shaft has a proximal portion and a distal portion. The distal portion has a taper angle greater than that of the proximal portion. The conical shaft has a plurality of flutes that extend along an outer surface thereof and terminate at the MTJ. The flutes define an outer diameter that has a constant taper angle along the entire length of the conical shaft. The dual taper of the conical shaft and the constant taper of the flutes results in deeper channels between the flutes at the distal portion than at the proximal portion. In addition, the flutes each have a width that is greater at the proximal portion than at the distal portion. This configuration provides strength at regions of higher stress while allowing for rotational stability along the shaft's entire length.

In one aspect of the present disclosure, a modular joint prosthesis includes a first component that has a body that defines a tapered opening therein, and a second component that has a trunnion and a shaft. The trunnion and shaft interface at a modular taper junction. The trunnion is tapered in a first direction toward a proximal end of the second component and is configured to be received within the tapered opening of the first component. The shaft is tapered in a second direction from the modular taper junction toward a distal end of the second component and has a proximal portion, a distal portion, and a plurality of flutes that are positioned about a longitudinal axis of the shaft and extend along an entire length of the shaft and terminate at the modular taper junction such that the flutes intersect the modular taper junction. The proximal portion defines a first minor diameter taper angle, the distal portion defines a second minor diameter taper angle greater than the first minor diameter taper angle, and the flutes define a major diameter of the shaft. The major diameter tapers at a major taper angle that is constant along the entire length of the shaft.

In another aspect of the present disclosure, a modular hip prosthesis includes a proximal body that has a neck configured to receive an artificial femoral head and defining a tapered opening. The prosthesis also includes an intramedullary stem that includes a trunnion that is tapered in a first direction toward a proximal end of the intramedullary stem and is configured to be received within the tapered opening of the proximal body, and a shaft that interfaces with the trunnion at a modular taper junction. The shaft is tapered in a second direction toward a distal end of the second component and has a proximal portion and a distal portion. The proximal portion and distal portion joining at a transition region. The proximal portion defines a first taper angle, and the distal portion defines a second taper angle. The second taper angle is greater than the first taper angle. A plurality of flutes extend outwardly from the conical shaft and along a length thereof such that the flutes extend over both the proximal and distal portions of the shaft. The flutes defining a third taper angle that is equal to the first taper angle.

In a further aspect of the present disclosure, an intramedullary stem prosthesis includes a trunnion tapered in a first direction toward a proximal end of the intramedullary stem, and a conical shaft interfacing with the trunnion at a modular taper junction. The conical shaft is tapered in a second direction toward a distal end of the second component and has a proximal portion, a distal portion, and flutes positioned about a longitudinal axis of the conical shaft and extending along an entire length of the conical shaft and terminating at the modular taper junction such that the flutes intersect the modular taper junction. The proximal portion defines a first taper angle, the distal portion defines a second taper angle greater than the first taper angle, and the flutes define a major diameter of the conical shaft. The major diameter tapers at a major diameter taper angle that is constant along the entire length of the conical shaft.

BRIEF DESCRIPTION OF THE DRAWINGS

The features, aspects, and advantages of the present invention will become better understood with regard to the following description, appended claims, and accompanying drawings in which:

FIG. 1A is a histogram of femoral canal isthmus diameters based on a bone database of a diverse population of human femoral bones.

FIG. 1B is a schematic cross-sectional view of a femur and a prior art prosthesis implanted therein.

FIG. 1C is a schematic cross-sectional view of a femur and another prior art prosthesis implanted therein.

DETAILED DESCRIPTION

Figure 2A:
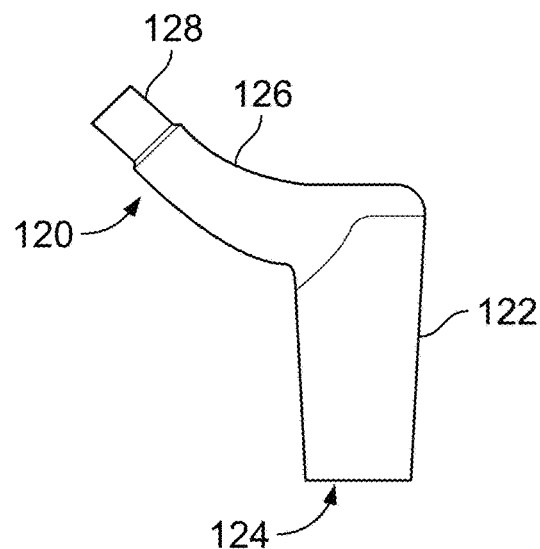
FIG. 2A is an exploded elevational view of a modular hip prosthesis according to an embodiment of the present disclosure.
Figure 2A:
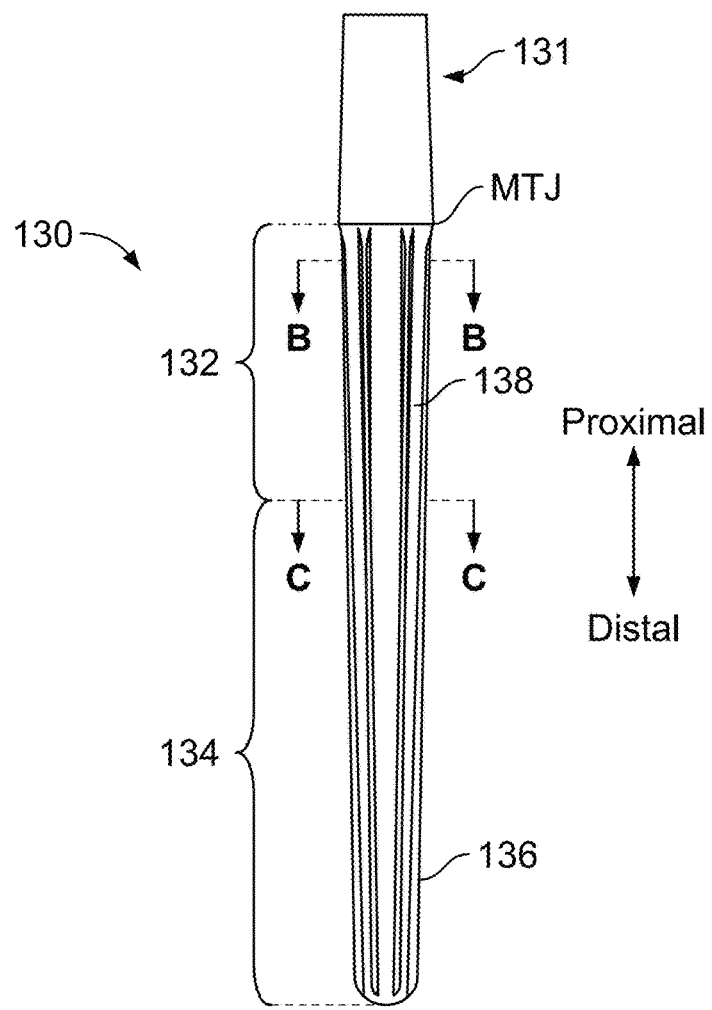

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that slight deviations from absolute are included within the scope of the term so modified.

FIGS. 2A-3F depict a modular hip prosthesis according to an embodiment of the present disclosure. The modular prosthesis generally includes a proximal body or metaphyseal component 120 and an intramedullary stem or diaphyseal component 130. Proximal body 120 generally includes a cone portion 122, a neck 126, and a trunnion 128. Trunnion 128 is positioned at a proximal end of neck 126 and is configured to connect to a femoral head prosthesis (not shown). However, in some embodiments, proximal body 120 may be provided with a femoral head integral with neck 126 such that neck 126 and the femoral head form a monolithic structure. Cone portion 120 has a porous outer surface 122 and has an inner surface that defines a tapered opening 124.

Intramedullary stem 130 is formed separately from proximal body 120 and generally includes a trunnion 131 and a conical shaft 138. Trunnion 131 defines a proximal end of intramedullary stem 130 and has a conical taper that tapers toward the proximal end such that a cross-sectional dimension of trunnion 131 at the proximal end is smaller than at a distal end thereof. Trunnion 131 is configured to be received within tapered opening 124 of proximal body 120 such that when trunnion 131 is received therein, a taper-lock is formed to secure cone 120 body to intramedullary stem 130.

Conical shaft 138 defines a distal end of intramedullary stem 130 and has a conical taper that tapers toward the distal end such that it has a smaller cross-sectional dimension at the distal end of shaft 138 than at a proximal end thereof, as best shown in FIGS. 3A-3E. The proximal end of conical shaft 138 joins with the distal end of trunnion 131 at an MTJ. In this regard, the MTJ defines a taper delineation in which structure (i.e., trunnion 131) at a proximal side of the MTJ tapers in a first direction and structure (i.e., conical stem 138) at a distal side of MTJ tapers in an opposite second direction.

Figure 3A:
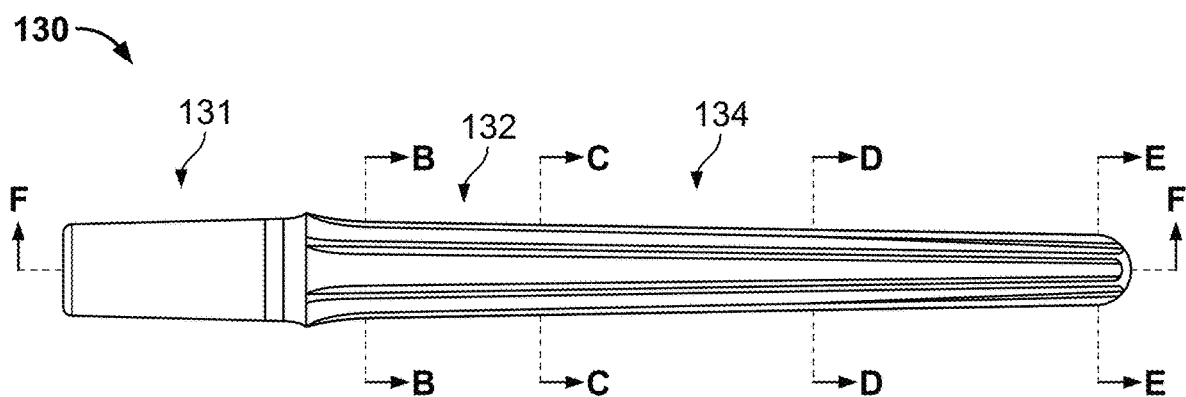
FIG. 3A is an elevational view of the stem of the prosthesis of FIG. 2A.
Figure 3B:
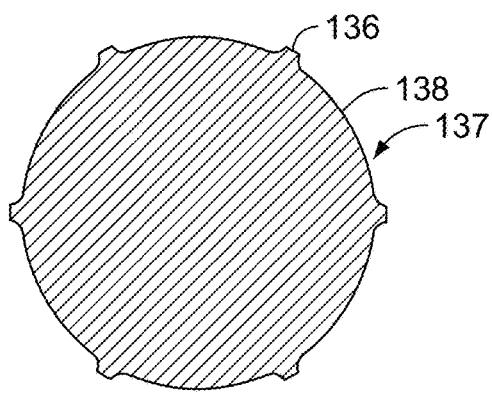
FIG. 3B is a cross-sectional view taken along line B-B of FIG. 3A.
Figure 3C:
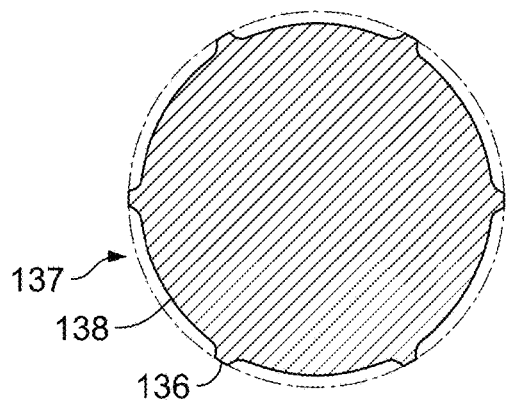
FIG. 3C is a cross-sectional view taken along line C-C of FIG. 3A.
Figure 3D:
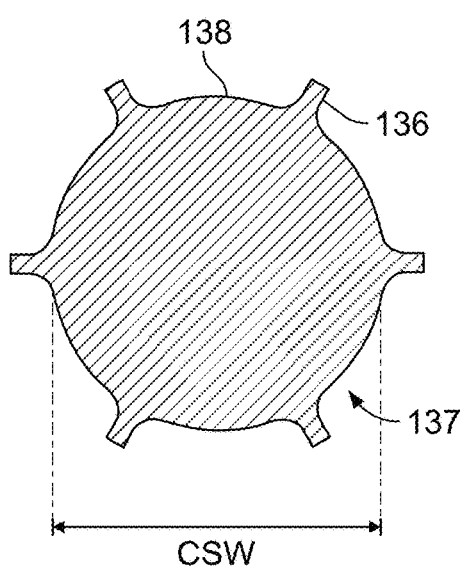
FIG. 3D is a cross-sectional view taken along line D-D of FIG. 3A.

Conical shaft 138 defines a minor diameter of intramedullary stem 130 (see FIG. 3E) and has a proximal portion or first portion 132 and a distal portion or second portion 134. While proximal portion 132 and distal portion 134 are both conically tapered, they have differing taper angles such that conical shaft 138 has a dual taper. In this regard, proximal portion 132 and distal portion 134 are separated by a first transition region "C," as best shown in FIGS. 2A, 3A, and 3F. Proximal portion 132 extends proximally from first transition region C, and distal portion 134 extends distally from transition region C. As best shown in FIG. 3F, proximal portion 132 has a first radius taper angle Q, and distal portion 134 has a second radius taper angle S. For example, taper angle Q is about 0.5 to 1.5 degrees, but preferably 1 to 1.5 degrees, and taper angle S is 1 to 2 degrees, but preferably 1.5 to 2 degrees. Thus, the overall minor diameter taper angle or inclusive taper angle of the proximal portion 132 is 2Q, or 1 to 3 degrees, but preferably 2 to 3 degrees, and the minor diameter taper angle or inclusive taper angle of distal portion 134 is 2S, or 2 to 4 degrees, but preferably 3 to 4 degrees. However, S and Q will generally be different from each other for each shaft embodiment such that the diameter taper angle of distal portion 134 is greater than that of proximal portion 132.

Intramedullary stem 130 is particularly suited for very small femurs, such as femurs that have an isthmus diameter of 10 mm or less. Such femurs are also generally shorter than most other femurs within a diverse population. Thus, the length of conical shaft 138 is also shorter than a conventional shaft. In this regard, conventional femoral shafts are about 155 mm from the MTJ to the distal end thereof. However, conical shaft 138 (i.e., the combined length of first and second portions 132, 134) is about 115 mm or shorter. In other words, the length of splined conical shaft 138 between the distal end thereof and the MTJ is about 115 mm or less.

Based on an analysis of a diverse population of femurs in a bone database, it has been determined that the average isthmus (or narrowest portion of femoral canal) is about 116 mm from the lesser trochanter, as can be seen in FIG. 1B. Therefore, the location of transition region C is located such that the minor diameter of shaft 138 is adapted to press-fit within the isthmus when fully implanted such that conical body 120 is in the desired position. In other words, when conical shaft 138 is inserted into an intramedullary canal of a femur, conical shaft 138 forms a taper-lock with the bone while flutes 136 extending therefrom penetrate into the bone. Thus, transition region C is located such that distal portion 134 will be positioned within the isthmus of whatever bone it is implanted into while proximal portion 132 is located in a region of the canal that widens from the isthmus. In this regard, transition region C is located at a length Lc from a distal end of intramedullary stem 130, as shown in FIG. 3F. This length Lc is about 35% or more of the total length of intramedullary stem 130 including trunnion 131. Alternatively expressed, transition region C is located at about 43% or more of the total length of shaft 138 (i.e., total length of proximal and distal portions 132, 134 excluding trunnion 131) from the distal end thereof. Thus, region C may be about 50 mm or greater from the distal end of shaft 138 where shaft 138 is 115 mm, for example. In another embodiment, length Lc may be 69% or more of the total length of shaft 138 from the distal end thereof. Thus, in such embodiment, region C may be 80 mm or greater from the distal end of shaft 138 where shaft is 115 mm, for example.

Conical shaft 138 is a fluted shaft and, therefore, includes a plurality of flutes or splines 136 that are positioned about a longitudinal axis of shaft 138 and that extend along a length thereof. In this regard, flutes 136 extend along the entire length of conical shaft 138 such that flutes 136 intersect and terminate at the MTJ. Each flute 136 is separated from an adjacent flute 136 by a groove or channel 137 which similarly extends along the entire length of shaft 138 and intersects and terminates at the MTJ. Thus, flutes 136 occupy as much of the length of shaft 138 as possible to ensure rotational stability along its entire length.

Figure 3E:
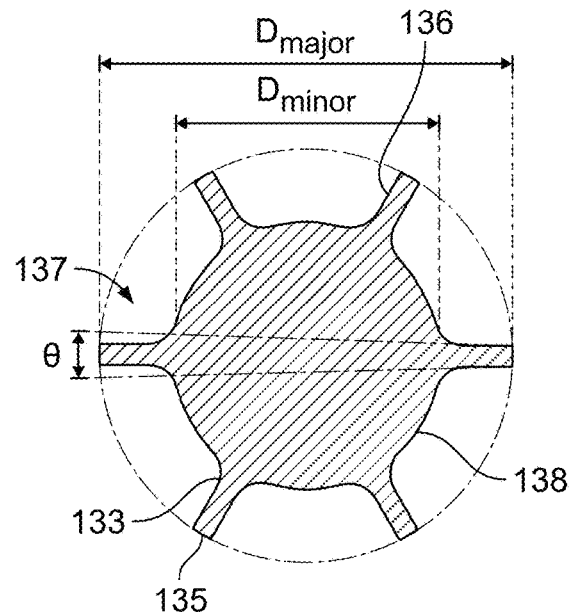
FIG. 3E is a cross-sectional view taken along line E-E of FIG. 3A.
Figure 3F:
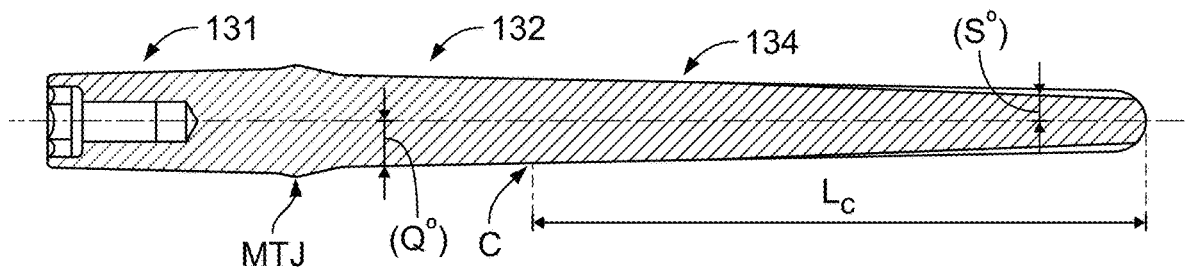
FIG. 3F is a cross-sectional view taken along line F-F of FIG. 3A.

Flutes 136 define a major diameter of shaft 138, as best shown in FIG. 3E. Flutes 136 taper along the entire length of shaft 138 such that the major diameter of shaft 138 gradually becomes smaller from the proximal end to the distal end thereof. In this regard, flutes 136 have a major diameter taper angle that is constant along the entire length of shaft 138. For example, the major diameter taper angle of flutes 136 may be 2 to 3 degrees. Such taper angle 136 may match that of a conventional reaming tool for preparing the femoral canal so that a customized tool need not be provided. In one embodiment, the diameter taper angle of flutes 136 is equal to the diameter taper angle of proximal portion 132. For example, the major diameter taper angle of flutes 136 and proximal portion 132 may be 2 degrees while the minor diameter taper angle of distal portion 134 may be 3 or 4 degrees. In such embodiment, flutes 136 would have a constant depth from a root 133 to a tip 135 thereof (see FIG. 3E) along proximal portion 132, but would have an increasing depth along distal portion 134 from first transition region C to the distal end of shaft 138. This configuration helps provide strength in the proximal portion 132 of shaft 138 where stress is the greatest while providing for rotational stability and sufficient fit within the isthmus of a very small canal.

Flutes 136 may also taper inwardly from root 133 to tip 135 to facilitate cutting into and passage through bone tissue. In this regard, flutes may each have a root-to-tip taper angle θ, as best shown in FIG. 3E. Such root-to-tip angle θ may be 2 to 5 degrees, but preferably 4 degrees.

Figure 2B:
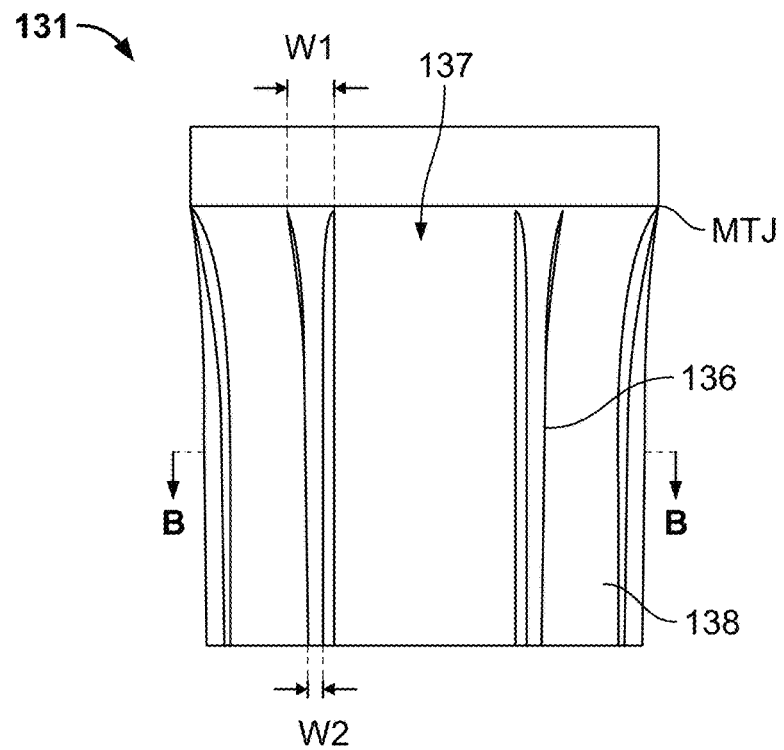
FIG. 2B is an enhanced view of a stem of the prosthesis of FIG. 2A.

Each flute 136 has a width, as shown in FIG. 2B, which is measured at the tip 135 of each flute 136. As shown, flutes 136 have a first maximum width W1 within proximal portion 132 and a second maximum width W2 within distal portion 134 of shaft 138. The first maximum width W1 is greater than the second maximum width W2. For example, the first maximum width W1 may be 1.5 mm to 2.0 mm and the second maximum width W2 may be 0.35 mm to 0.75 mm. This difference helps bolster the strength of proximal portion 132 against cyclic loading which realizes the greatest fatigue stress during use.

In one embodiment, the width of flutes 136 at the distal portion 134 are constant along the entire length thereof and then flare outwardly to a maximum overall width (i.e., W1) at the MJT. In this embodiment, the width of flutes 136 begins the transition from a constant width to the maximum overall width at a second transition region "B," as best shown in FIGS. 2A-3A. Such transition region B is shown as being more proximal than the first transition region C. However, second transition region B may be co-located with first transition region C. In an alternative embodiment, the width of flutes 136 may be constant along the length of proximal portion 132, while tapering outwardly from the distal end of shaft 138 along distal portion 134 from the distal end thereof to transition region B.

In another embodiment, the width of flutes 136 may gradually increase from the distal end of shaft 138 and then rapidly increase to the maximum width W1 at second transition region B. In this regard, the width of flutes 136 may have a first flute taper angle along distal portion 134 of shaft 138 and a second flute taper angle along proximal portion 132. The second flute taper angle may be greater than the first flute taper angle. In other words, the width of flutes 136 expand at a greater rate along proximal portion 132 than distal portion 134.

In a further embodiment, the width of each flute 136 may increase from the distal end of shaft 138 to the first transition region C at a first flute taper angle and from the second transition region B to the MTJ at a second flute taper angle. In such embodiment, the second flute taper angle may be larger than the first flute taper angle. However, the width of flutes 136 may be constant between the first transition region C and the second transition region B. Thus, where transition regions B and C are co-located, the result is the embodiment described in the paragraph above.

In yet another embodiment, the width of each flute 136 may be constant from the distal end of shaft 138 to the first transition region C and from the second transition region B to the MTJ. However, flutes 136 may gradually increase in width from transition region C to transition region B.

As mentioned above, the increased width of the proximal flutes 136 helps bolster the strength of proximal portion 132. In this regard, the increased width of flutes 136 operates in conjunction with the decreased depth of grooves 137 (i.e., increased minor diameter of shaft 138) within proximal portion 132 to increase the cross-sectional area or polar moment of inertia of shaft 138 within this region so that it can effectively resist cyclical loads.

As mentioned above, intramedullary stem 130 is particularly suited for very small intramedullary canals. In this regard, intramedullary stem 130 has a nominal diameter that is 11 mm to 16 mm Such nominal diameter is determined by the major diameter of the intramedullary stem 130 at 120 mm from the distal end of shaft 138. However, as also mentioned above, shaft 138 is 115 mm or less in length. Thus, the nominal diameter of intramedullary stem 130 is based upon a theoretical major diameter of shaft 138 if shaft 138, including flutes 136, were extended to 120 mm or more. In addition, the maximum major diameter of shaft 138 that is 115 mm or less in length is 14 mm. Also, as shown in FIG. 3D, shaft 138 has a cross section width ("CSW") as measured between flutes 136 and at grooves 137. Such CSW, also described as minor diameter, varies along the length of shaft 138 due to the tapering minor diameter discussed above. When stem 130 is implanted into bone, flutes 136 cut into the bone, while shaft 138 may abut an interior surface of the bone in a press-fit manner Thus, to help ensure shaft 138 can fit within very small intramedullary canals, the maximum CSW of shaft 138 is 13.5 mm. However, such maximum CSW of shaft 138 would also be the maximum CSW of proximal portion 132. Distal portion 134 includes the minimum CSW, which is located at cross-section E-E of FIGS. 3A and 3E, and is 3 mm to 8 mm.

Figure 4B:
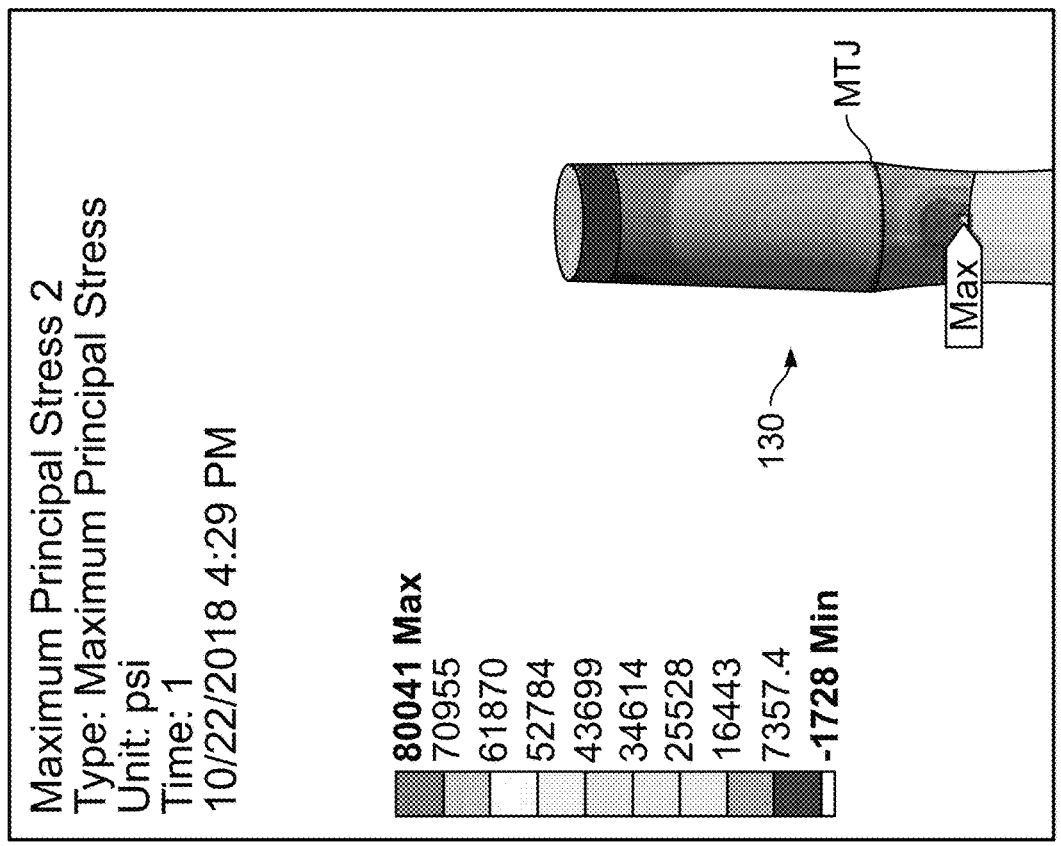
FIG. 4B is a heat map of stress within the stem of the prosthesis of FIG. 2A under a load applied in a finite element analysis.
Figure 4A:
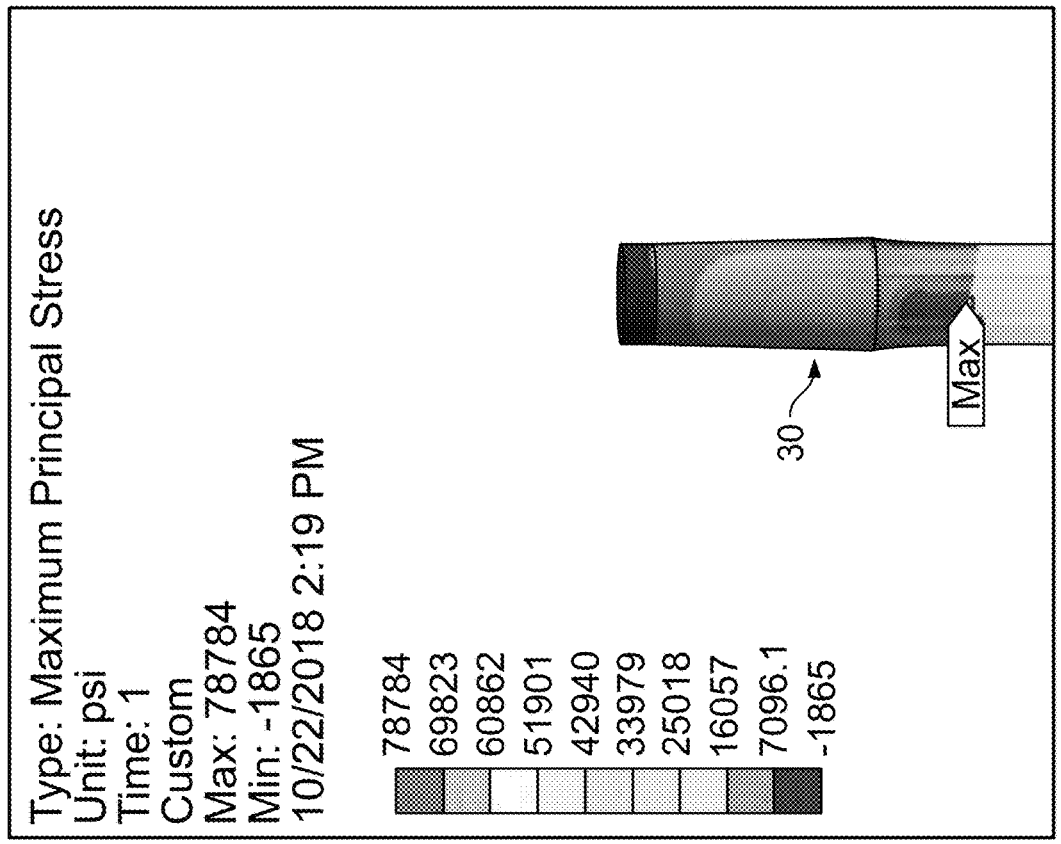
FIG. 4A is a heat map of stress within a prior art stem under a load applied in a finite element analysis.

FIG. 4A depicts a heat map illustrating the stress distribution in a proximal end of the conventional intramedullary stem 30 of FIG. 1B based on an expected operating load. As mentioned above with respect to FIG. 1B, although intramedullary stem 30 has flutes 36 extending along an entire length of shaft 38, it is too large to fit within very small femoral canals and, if scaled down, would not be functional in a very small femoral canal while maintaining flutes 36 at the proximal end of conical shaft 38 due to strength concerns. In this regard, the features of intramedullary stem 130 described herein allows stem 130 to have sufficient strength in regions of highest stress while also allowing flutes 136 to extend along the entire length of conical shaft 138 for rotational stability. This strength is illustrated in FIG. 4B in which the maximum principal stress seen in intramedullary stem 130 is comparable to stem 30 under the same loading conditions as that presented in FIG. 4A.

Although proximal body 120 and intramedullary stem 130 are described as modular such that proximal body 120 is connectable to intramedullary shaft 130, it is contemplated that the features described herein can also be applied to a monolithic implant in which proximal body 120 is integral with intramedullary shaft 130. In this regard, flutes 136 would extend along the entire length of the intramedullary stem 130 until they reach an interface with the integral proximal body 120.

In even further embodiments, the features described herein can be applied to other categories of prostheses. For example, intramedullary stem 130 can be adapted to be connected to and in conjunction with a humeral head component for a shoulder replacement or a femoral component for a knee replacement.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A modular joint prosthesis comprising:
    a first component having a body defining a tapered opening therein; and
    a second component having a trunnion and a shaft, the trunnion and shaft interfacing at a modular taper junction, the trunnion being tapered in a first direction toward a proximal end of the second component and configured to be received within the tapered opening of the first component, the shaft being tapered in a second direction from the modular taper junction toward a distal end of the second component and having a proximal portion, a distal portion, and a plurality of flutes positioned about a longitudinal axis of the shaft and extending along an entire length of the shaft and terminating at the modular taper junction such that the flutes intersect the modular taper junction, the proximal portion defining a first minor diameter taper angle that is non-zero, the distal portion defining a second minor diameter taper angle greater than the first minor diameter taper angle, and the flutes defining a major diameter of the shaft, wherein the major diameter tapers at a major taper angle that is constant along the entire length of the shaft.

2. The prosthesis of claim 1, wherein the flutes each have a maximum width along the proximal portion that is greater than a maximum width along the distal portion.

3. The prosthesis of claim 1, wherein each flute is separated from an adjacent flute by a groove, the groove intersecting the modular taper junction such that the adjacent flutes are separated by the groove at the modular taper junction.

4. The prosthesis of claim 1, wherein a maximum major diameter of the shaft is 14 mm.

5. The prosthesis of claim 1, wherein a maximum minor diameter of the shaft is 13.5 mm.

6. The prosthesis of claim 1, wherein the proximal portion and distal portion intersect at a first transition region that is 43% of the length of the shaft or more from the distal end of the shaft.

7. The prosthesis of claim 6, wherein the maximum length of the shaft is 115 mm.

8. The prosthesis of claim 6, wherein the width of the flutes is constant along the distal portion and begin to widen to their respective maximum width along the proximal portion at a second transition region.

9. The prosthesis of claim 6, wherein the width of the flutes increases at a first flute taper angle from a distal end of the shaft to the first transition region and at a second flute taper angle from the first transition region to the modular taper junction, the second flute taper angle being greater than the first flute taper angle.

10. The prosthesis of claim 6, wherein the width of the flutes increases at a first flute taper angle from a distal end of the shaft to the first transition region and at a second flute taper angle from a second transition region to the modular taper junction, and the width of the flutes is constant from the first transition region to the second transition region.

11. The prosthesis of claim 1, wherein the maximum width of the flutes along the distal portion is 1.7 mm and the maximum width of the flutes along the proximal portion is 0.4 mm.

12. The prosthesis of claim 1, wherein the first minor taper angle of the proximal portion is equal to the major diameter taper angle.

13. The prosthesis of claim 1, wherein the first minor taper angle is 2 degrees and the second minor taper angle is 3 to 4 degrees.

14. The prosthesis of claim 13, wherein the major diameter taper angle is 2 degrees.

15. The prosthesis of claim 1, wherein the flutes taper from a root to a tip thereof at a root-to-tip taper angle.

16. The prosthesis of claim 15, wherein the root-to-tip taper angle is 4 degrees.

17. A modular hip prosthesis comprising:
a proximal body having a neck configured to receive an artificial femoral head and defining a tapered opening;
an intramedullary stem having:
a trunnion being tapered in a first direction toward a proximal end of the intramedullary stem and configured to be received within the tapered opening of the proximal body,
a shaft interfacing with the trunnion at a modular taper junction, the shaft being tapered in a second direction toward a distal end of the intramedullary stem and having a proximal portion and a distal portion, the proximal portion and distal portion joining at a transition region, the proximal portion defining a first taper angle, the distal portion defining a second taper angle, wherein the second taper angle is greater than the first taper angle, and
a plurality of flutes extending outwardly from the shaft and along a length thereof such that the flutes extend over both the proximal and distal portions of the shaft, the flutes defining a third taper angle that is equal to the first taper angle.

18. The prosthesis of claim 17, wherein the first taper angle is 2 degrees and the second taper angle is 3 to 4 degrees.

19. The prosthesis of claim 17, wherein the flutes have a first maximum width along the proximal portion and a second maximum width along the distal portion, the first maximum width being greater than the second maximum width.

20. An intramedullary stem prosthesis comprising:
a trunnion being tapered in a first direction toward a proximal end of the intramedullary stem prosthesis; and
a conical shaft interfacing with the trunnion at a modular taper junction and having a length of 115 mm or less, the conical shaft being tapered in a second direction toward a distal end of the intramedullary stem prosthesis and having a proximal portion, a distal portion, and a plurality of flutes positioned about a longitudinal axis of the conical shaft and extending along an entire length of the conical shaft and terminating at the modular taper junction such that the flutes intersect the modular taper junction, the proximal portion defining a first taper angle, the distal portion defining a second taper angle greater than the first taper angle, and the flutes defining a major diameter of the conical shaft, wherein the major diameter tapers at a major diameter taper angle that is constant along the entire length of the conical shaft.

* * * * *